(12) United States Patent
Pickett et al.

(10) Patent No.: US 8,343,212 B2
(45) Date of Patent: Jan. 1, 2013

(54) POLYMER COATINGS ON MEDICAL DEVICES

(75) Inventors: Christopher John Pickett, Cambridge (GB); Timothy James Boote, Cambridge (GB); Saad Khalil Ibrahim, Cambridge (GB); Jane Marie Knott, Cambridge (GB); John Douglas Tolland, Cambridge (GB)

(73) Assignee: Biotectix, LLC, Boston, MA (US)

( * ) Notice: Subject to any disclaimer, the term of this patent is extended or adjusted under 35 U.S.C. 154(b) by 288 days.

(21) Appl. No.: 12/599,865

(22) PCT Filed: May 15, 2008

(86) PCT No.: PCT/GB2008/001675
§ 371 (c)(1),
(2), (4) Date: Nov. 12, 2009

(87) PCT Pub. No.: WO2008/139200
PCT Pub. Date: Nov. 20, 2008

(65) Prior Publication Data
US 2010/0312331 A1   Dec. 9, 2010

(30) Foreign Application Priority Data

May 15, 2007  (GB) .................................. 0709332.1
Oct. 3, 2007   (GB) .................................. 0719321.2

(51) Int. Cl.
| A61L 27/10 | (2006.01) |
| A61F 2/00  | (2006.01) |
| B05D 7/24  | (2006.01) |
| B05C 3/02  | (2006.01) |

(52) U.S. Cl. ......... 623/2.1; 252/500; 424/400; 424/422; 424/423; 428/411.1; 428/461; 623/1.1; 623/3.1; 623/11.11; 623/900; 623/902; 623/924

(58) Field of Classification Search .................. 252/500; 428/411, 461; 424/400, 422, 423; 623/2.2, 623/2.1, 3.1, 11.11, 900, 902, 924; 604/403
See application file for complete search history.

(56) References Cited

U.S. PATENT DOCUMENTS

| 4,917,921 A | 4/1990 | Hermes |
| 6,050,980 A | 4/2000 | Wilson |
| 6,468,304 B1 | 10/2002 | Dubois-Rande et al. |
| 6,517,858 B1 | 2/2003 | Le Moel et al. |
| 2003/0099684 A1 | 5/2003 | Domb |
| 2003/0157142 A1 | 8/2003 | Nagel et al. |
| 2004/0014936 A1 | 1/2004 | Grunze et al. |
| 2004/0234575 A1 | 11/2004 | Horres et al. |
| 2004/0253467 A1 | 12/2004 | Schüssler et al. |

FOREIGN PATENT DOCUMENTS

| DE | 19613048 | 10/1996 |
| DE | 19604173 | 8/1997 |
| DE | 102005018356 | 10/2006 |
| EP | 0 679 373 | 11/1995 |
| EP | 1 444 993 | 8/2004 |
| EP | 1 504 775 | 2/2005 |
| JP | 2006 271888 | 10/2006 |
| WO | WO 98/36784 | 8/1998 |
| WO | WO 98/46286 | 10/1998 |
| WO | WO 99/52574 | 10/1999 |
| WO | WO 99/64086 | 12/1999 |
| WO | WO 00/16764 | 3/2000 |
| WO | WO 01/39813 | 6/2001 |
| WO | WO 01/91918 | 12/2001 |
| WO | WO 02/20062 | 3/2002 |
| WO | WO 02/056904 | 7/2002 |
| WO | WO 03/007687 | 1/2003 |
| WO | WO 03/008006 | 1/2003 |
| WO | WO 03/018082 | 3/2003 |
| WO | WO 03/039768 | 5/2003 |
| WO | WO 03/041755 | 5/2003 |
| WO | WO 03/093357 | 11/2003 |
| WO | WO 2004/028406 | 4/2004 |
| WO | WO 2005/027990 | 3/2005 |
| WO | WO 2005/049103 | 6/2005 |
| WO | WO 2005/069966 | 8/2005 |
| WO | WO 2005/107828 | 11/2005 |
| WO | WO 2005/113031 | 12/2005 |
| WO | WO 2005/115489 | 12/2005 |
| WO | WO 2005/115496 | 12/2005 |
| WO | WO 2005/118018 | 12/2005 |
| WO | WO 2006/008739 | * 1/2006 |
| WO | WO 2006/022920 | 3/2006 |
| WO | WO 2006/049913 | 5/2006 |

(Continued)

OTHER PUBLICATIONS

Le Gall, T. et al., "Synthesis of N-derivatised pyrroles: precursors to highly functionalised electropolymers", J. Chem. Soc. Perkin Trans.; 1999; 1; pp. 1657-1664.

Rose, Peter et al., "Bioactive S-alk(en)yl cysteine sulfoxide metabolites in the genus Allium: the chemistry of potential therapeutic agents", Nat. Prod. Rep.; 2005; 22; pp. 351-368.

Kiesewetter, H. et al., "Effect of garlic on platelet aggregation in patients with increased risk of juvenile ischaemic attack", J. Clin. Pharm.; 1993; 45(4); pp. 333-336.

Pickett, Christopher J. et al., "Bioinorganic Reaction Centres on Electrodes. Modified Electrodes possessing Amino Acid, Peptide and Ferredoxin-type Groups on a Poly(pyrrole) Backbone", J. Chem. Soc. Dalton Trans.; 1994; 14; pp. 2181-2189.

(Continued)

Primary Examiner — Ana Woodward
(74) Attorney, Agent, or Firm — Senniger Powers LLP

(57) ABSTRACT

A medical device, for example a stent, has a surface which in use contacts body tissue, wherein said surface has on it a biocompatible coating layer comprising a polymer having covalently bound allyl-terminated pendent groups, said pendent groups comprising a moiety selected from $-O-CH_2-CH=CH_2$, $-S-CH_2-CH=CH_2$, $-S(=O)-CH_2-CH=CH_2$, $-Se-CH_2-CH=CH_2$ and $-Se(=O)-CH_2-CH=CH_2$. This surface has good biocompatibility and can bind strongly to a metallic surface. The polymer may be made from an electropolymerisable monomer, e.g. a pyrrole.

14 Claims, 2 Drawing Sheets

FOREIGN PATENT DOCUMENTS

| WO | WO 2006/065685 | 6/2006 |
|----|----|----|
| WO | WO 2006/069677 | 7/2006 |
| WO | WO 2006/086672 | 8/2006 |
| WO | WO 2006/099409 | 9/2006 |
| WO | WO 2007/003516 | 1/2007 |

OTHER PUBLICATIONS

Frank, Rolf Dario, et al., "*Glutardialdehyde induced fluorescence technique (GIFT): A new method for the imaging of platelet adhesion on biomaterials*", J. Biomed. Mat. Research; 2000; 52; pp. 374-381.

Ko, Tze-Man et al., "*Surface characterization and platelet adhesion studies of plasma-sulphonated polyethylene*", Biomaterials, 1993; 14(9); pp. 657-664.

Blume, R.C., et al., "*Formylation and Cyanoethylation of Substituted Indoles*", J. Org. Chem.; 1945; 10(3); pp. 255-258.

Kashiwagi, Y. et al., "*Polypyrrole-Supported Graphite Felt for Acetylene Coupling Reaction in Solid Phase*", Synlett.; 2004; 14; pp. 2513-2516.

Weiss, Z. et al., "*Pyrrole Derivatives for Electrochemical Coating of Metallic Medical Devices*", J. Polym. Sci.; 2004; 42; pp. 1658-1667.

Okner, R. et al., "*Electrocoating of stainless steel coronary stents for extended release of Paclitaxel*", Mat. Sci. & Eng.; 2007; 27; pp. 510-513.

Gunn, J. et al., "*Stent coatings and local drug delivery*", Euro. Heart J.; 1999; 20; pp. 1693-1700.

Widge A. S. et al., "*Self-assembled monolayers of polythiophene conductive polymers improve biocompatibility and electrical impedance of neural electrodes*", Biosensors & Bioelectronics; 2007; 22; pp. 1723-1732.

Matsuhashi, T. et al., "In Vivo *Evaluation of a Fluorine-Acryl-Stylene-Urethane-Silicone Antithrombogenic Coating Material Copolymer for Intravascular Stents*", Acad. Radiol.; 1996; 3; pp. 581-588.

International Search Report and Written Opinion of the International Searching Authority for International Patent Application No. PCT/GB2008/0011675, Aug. 20, 2009, European Patent Office, Rijswijk, Netherlands.

European Examination Report for European Patent Application No. 08 750 607.7, Feb. 18, 2011, European Patent Office, Rijswijk, Netherlands.

* cited by examiner

Monolayer of human artery endothelial cells on surface of poly E

POLYMER COATINGS ON MEDICAL DEVICES

FIELD OF THE INVENTION

The present invention relates to polymer coatings on medical devices.

BACKGROUND OF THE INVENTION

In the field of medicine, many devices are employed which contact body tissue and fluids. These include for example implanted devices, components of blood dialysis devices and blood storage containers. It is important that the surfaces which contact body tissue have certain properties to make them suitable for their function. One of the most important of these is biocompatibility, and non-toxicity to cells. When the device is intended for contact with blood, it is important that the surface of the device does not induce thrombosis. Other considerations are important, depending on the intended use of the device.

For example, in the case of coronary stents, it is desirable that the surface of the stent does not induce inflammatory response, does not promote thrombosis and is rapidly endothelialised. In earlier practice, bare metal stents made from medical steel or other alloys in various designs were predominantly used in coronary stenting procedures. However, following the arterial vessel damage inevitably associated with the stenting operation, smooth muscle cell proliferation and migration into the lumen occurs. This is called restenosis. In 15-20% of operations using a bare metal stent, restenosis leads to serious loss of lumen volume. This requires further medical intervention, commonly re-stenting of the vessel.

In recent years, coronary stents have been modified with polymer coatings which are loaded with drugs, commonly paclitaxel, rapamycin and closely related drugs. These drugs elute from the polymer and inhibit cell migration and neointimal thickening of the arterial wall. Such devices are known as drug-eluting stents. The use of such stents has led to a dramatic reduction in the occurrence of restenosis.

However, certain concerns about the safety of drug-eluting stents have emerged. Late-onset thrombosis leading to death occurs in some patients between 1 and 4 years after implantation of drug eluting stents. For this reason, the proportion of drug eluting stents used in coronary stenting operations has declined in favour of bare metal stents.

The cause of this late onset thrombosis is likely to be that the polymer coating or the combination of polymer and residual drug induces an inflammatory response, leading to platelet adhesion and activation, which triggers the thrombogenic cascade. Paclitaxel and rapamycin diminish restenosis, but they also inhibit endothelial cell proliferation which is necessary for healing of the damaged artery and is protective against thrombosis.

In the light of these problems, the aim of the present invention is to provide improved biocompatible polymeric coatings on stents and other medical devices which are in contact with body tissue.

It is known that extracts of *Allium sativum* (garlic) have a platelet inhibiting effect (1). In a double-blind, placebo-controlled study on 60 voluntary subjects with cerebrovascular risk factors and constantly increased platelet aggregation, it was demonstrated that the daily ingestion of 800 mg of powdered garlic (in the form of coated tablets) over four weeks led to a significant inhibition of the pathologically increased ratio of circulating platelet aggregates and of spontaneous platelet aggregation.

Some of the compounds in extracts of garlic with anti-inflammatory and platelet inhibiting effects are ajoene, allicin, alliin and ethiin, shown below

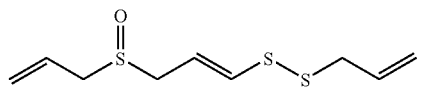

Ajoene

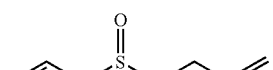

Allicin

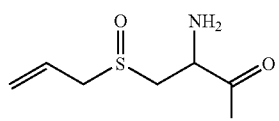

Alliin

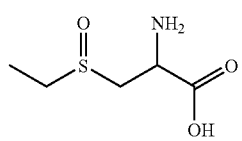

Ethiin

See: Bioactive S-alk(en)yl cysteine sulfoxide metabolites in the genus *Allium*: the chemistry of potential therapeutic agents.

P. Rose, M. Whiteman, P. K. Moore and Y Z Zhu.

Nat. Prod. Rep., 2005, 22, 351-368

WO03/018082 discloses an implantable medical device, such as a stent, comprising a substrate and a biocompatible polymeric coating, wherein the coating contains ajoene and/or allicin or isomers, analogues, homologues or derivatives thereof. The biocompatible coating has a composition which permits the ajoene and/or allicin to be controllably released in a predetermined manner and over a prolonged period of time. Therefore, the medical devices disclosed in this document are in the "drug-eluting" category.

U.S. Pat. No. 4,917,921 discloses antithrombogenic and antibiotic compositions for use as coatings on artificial prostheses and implants which remain in contact with blood or other physiological fluids. The compositions are copolymers of 2-vinyl-4H-1,3-dithiin with a biocompatible monomer. The dithiin is a garlic extract having an allyl functionality. Thermal initiation using free-radical initiators, photochemical initiation using photoinitiators, or chemical initiation using group transfer polymerisation with activated methylmethacrylate are disclosed as possible routes for generating the copolymer. The allyl group is the polymerising part of the monomer, and is therefore not present in the polymer.

The monomer

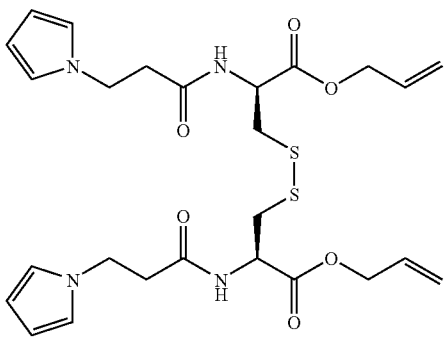 [SMILES: C=CCOC(=O)[C@H](CSSC[C@@H](NC(=O)CCn1cccc1)C(=O)OCC=C)NC(=O)CCn1cccc1]

has been disclosed, as an intermediate in a synthesis of other derivatised pyrroles (2). It is mentioned that this intermediate, along with a number of others, is electropolymerisable.

SUMMARY OF THE INVENTION

The object of the present invention is to provide medical devices with improved biocompatible polymeric coatings.

According to the present invention, there is provided a medical device having a surface which in use contacts body tissue, wherein said surface has on it a biocompatible coating layer comprising a polymer having covalently bound allyl-terminated pendent groups, said pendent groups comprising a moiety selected from

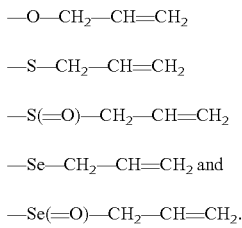

Medical devices according to the present invention can provide a number of advantages. For example, they may have low platelet adhesion and platelet activation properties, and so may be non-thrombogenic or anti-thrombogenic. They may support endothelialisation, so promote the healing process after implantation. They may have low cytotoxicity, may be haemocompatible and are generally well tolerated in biological systems. The coating layer may also exhibit strong adhesion to metallic surfaces.

The coating layer may include a drug, incorporated in a releasable or non-releasable manner. The drug may be bound to the polymer by for example covalent bonding, ionic bonding, coordinate bonding, or attached by a weak interaction such as hydrogen bonding or Van der Waal's force.

It is thought to be the allyl-terminated pendent groups in the polymeric coatings on medical devices according to the present invention which confer the beneficial effects, augmented by neighbouring O, S or Se atom. Therefore, in principle the nature of the polymer is not limited in the present invention, except that pendent groups comprising a moiety selected from those given above must be present. Examples of possible polymers are polypyrroles, polythiophenes, polyanilines, polyamides, poly-aminoacids, polysaccharides, polyesters, polyalkenes, polyamines, polyethers, polyethyleneterephthalates, polyimides, polysiloxanes, polyphosphazines, polylactides, polyglycolides, polycaprolactones, polydioxanones, polygluconates, polyanhydrides, polyphosphoesters, polyorthoesters and polyphosphate esters. Polymeric coatings on medical devices according to the present invention may comprise copolymers.

Polymers according to the present invention include polymers of two or more types of monomer, in which one or more of the types of monomeric residue includes the allyl terminated pendent group. Preferably at least 10%, more preferably at least 30%, of the monomeric residues in the polymer include the allyl terminated pendent group. Yet more preferably, at least 50% of the monomeric residues in the polymer include the allyl terminated pendent group. Even more preferably, at least 70% of the monomeric residues in the polymer include the allyl terminated pendent group. 100% of the monomeric residues in the polymer may include the allyl terminated pendent group.

The polymeric coatings on medical devices of the present invention may be formed by any polymerisation method, including electropolymerisation, ring-opening polymerisation, radical polymerisation, coordination polymerisation, functional group (step growth) polymerisation, metathesis polymerisation and cationic polymerisation. The allyl-terminated pendent group may be present in the monomer prior to polymerisation. If necessary, the allyl-terminated pendent group may be protected during polymerisation, for example by attaching a protecting group. Alternatively, the allyl-terminated pendent group may be covalently bonded to the polymer after polymerisation.

Preferably, the polymeric coatings on medical devices according to the present invention are electropolymerised. This is because allyl groups in monomers are not involved in polymerisation when the polymerisation is electropolymerisation, so it is facile to ensure that the allyl pendent group remains present in the polymer product. Therefore, preferably the polymer or polymers forming the polymeric coating on a medical device according to the present invention are selected from polypyrroles, polythiophenes and polyanilines. Most preferably, the polymeric coating according to the present invention comprises a polypyrrole.

It is believed that the presence of an allyl terminal group in the pendent groups confers the beneficial properties of medical devices having polymeric coatings according to the present invention. The pendent groups comprise a moiety selected from:

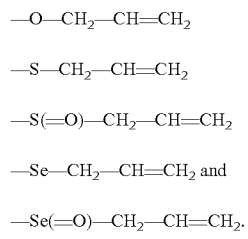

More preferably, the pendent groups comprise a moiety selected from:

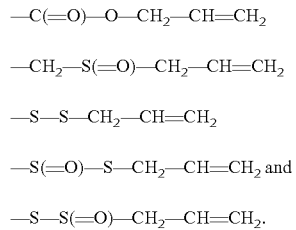

The pendent groups are covalently attached, directly or via a linker, to the polymeric chain (backbone). The nature of the attachment is not crucial in conferring the beneficial properties of the invention. Typically, the pendent groups are attached to the residue of the polymerisable component of the monomer. For example:

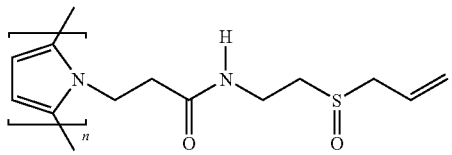

where the pendent group is attached to the pyrrole ring residue in the polypyrrole polymer.

When the polymer is a polypyrrole the pendent groups may be attached, directly or via a linker, to N atoms in the pyrrole rings, or to C atoms in the 3-position in the pyrrole rings. Preferably, the pendent groups are attached to N atoms in the pyrrole rings.

When the polymer is a polythiophene the pendent groups may be attached, directly or via a linker, to C atoms in the 3-position in the thiophene rings.

When the polymer is a polyaniline the pendent groups may be attached, directly or via a linker, to the aromatic ring.

The pendent groups are covalently attached to the polymer in polymeric coatings on medical devices according to the present invention. There may be a direct covalent bond between a pendent group selected from those listed above and the polymer. However, preferably the pendent groups are attached to the polymer via a covalent linker. The linker is not limited in the present invention. It may be a saturated or unsaturated alkyl moiety. Preferably, the covalent linker comprises a moiety selected from amido, ester and ether. More preferably, the covalent linker comprises a moiety selected from amido or ester. Most preferably, the covalent linker comprises an amido moiety. When the covalent linker comprises an amido moiety, it is preferable that the pendent group is closer to the N atom of the amido moiety than to the C atom of the amido moiety.

Typically a monomer for forming polymeric coatings on implantable devices according to the present invention can be defined as

A-B-C-D-E where:

A is the polymerisable component, for example a pyrrole ring, a thiophene ring or an aniline ring;

B is $C_{1-20}$ alkyl chain. The alkyl chain may be branched or unbranched, and optionally substituted;

C is amido (—CO—NH—), ester (—CO—O—) or ether (—O—), preferably amido;

D is $C_{1-20}$ alkyl chain. The alkyl chain may be branched or unbranched, and optionally substituted; and E is the pendent group.

Components B and D are each optional.

Components A, B (if present), C, D (if present) and E are covalently attached as shown above. Components B (if present), C and D (if present) together are the covalent linker.

Preferred optional substituents on B and/or D, when present, are any of

—COOH or —COO⁻
—COOR'
—CONH$_2$
—CONHR'
—CON(R')$_2$
—COR'
—F, —Cl, —Br, —I

—CN
—NO$_2$
—OH
—OR'
—SH
—SR'
—O—CO—R'
—NH$_2$
—NHR'
—NH(R')$_2$
N(R')$_3^+$ e.g. (N(CH$_3$)$_3^+$
—NH—CO—R'
—NH—CO—H
—NR'—CO—R'
—NR'—SO$_2$H
—NR'—SO$_2$R'
—SO$_2$R'
—OSO$_2$R'
—C$_{5-20}$aryl
—C$_{1-7}$alkyl-C$_{5-20}$aryl
—C$_{1-7}$alkenyl-C$_{5-20}$aryl, wherein R' is alkyl or alkenyl of 1 to 6 C atoms, preferably 1 to 4 C atoms.

Preferably D is unsubstituted, or is substituted by a charged group such as —COO⁻ or N(R')$_3^+$ e.g. N(CH$_3$)$_3^+$ which may bind a charged drug moiety. The covalent linker or pendent group may be covalently attached to another covalent linker or pendent group. An example of a monomer for forming polymeric coatings on medical devices according to the present invention is:

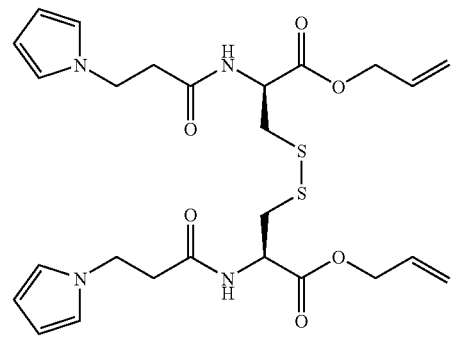 [SMILES: C=CCOC(=O)[C@H](CSSC[C@@H](NC(=O)CCn1cccc1)C(=O)OCC=C)NC(=O)CCn1cccc1]

Medical devices according to the present invention have a surface which in use contacts body tissue, wherein said surface has on it a biocompatible coating layer comprising a polymer as described above. The medical device may be one of a stent, an orthopaedic implant, a pump, a heart valve, a blood dialysis device, a blood storage container and a catheter guide wire. Preferably, the medical devices according to the present invention are adapted to be implanted into a mammalian body. Preferably, they are adapted to be in contact with blood. Most preferably, the medical device is a stent. The invention is applicable to devices used in veterinary medicine. The invention extends to devices used in blood storage and blood treatment, for example of blood to be used in transfusion.

DEFINITIONS

The term "electropolymerised" as used herein pertains to a polymer which is formed by the electropolymerisation of electropolymerisable monomers. They are synthesised by applying a potential across a solution of the monomer.

When referring to a type of polymer, for example "polypyrroles", the term "polypyrroles" (or equivalent), as used herein, pertains to derivatives of polypyrrole, insofar as the such polymers are not excluded by other limitations. For example, polymers according to the present invention must have pendent groups according to the present invention.

The term "body tissue" as used herein pertains to a collection of viable cells which are within a living body or are intended to be put into a living body. The term includes body fluids, such as blood.

DETAILED DESCRIPTION

Figure 1:
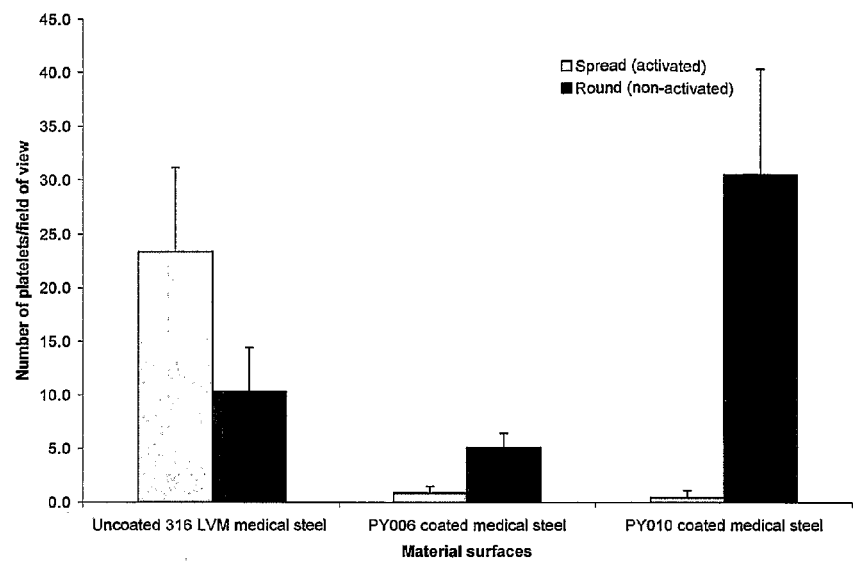
FIG. 1 shows the platelet shape distribution of human platelets adhering to uncoated and coated medical steel surfaces.

In the following description, polymers of the following monomers are referred to. The polymer of monomer A is referred to as "poly A", the polymer of monomer E as poly E, etc.

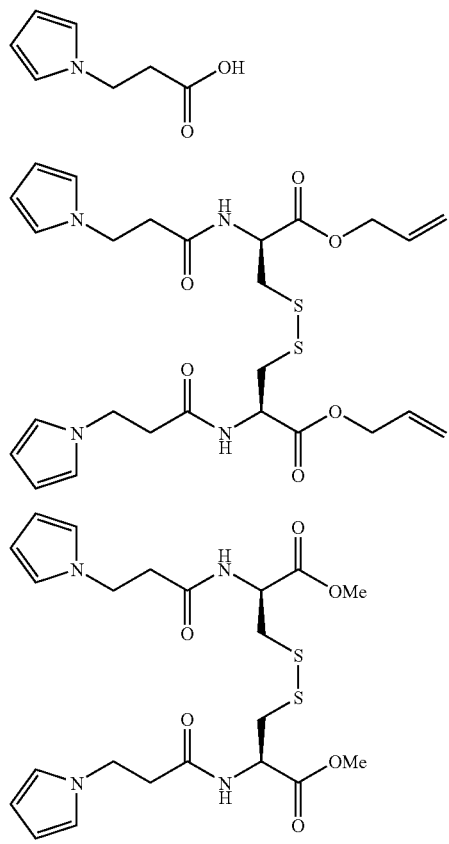

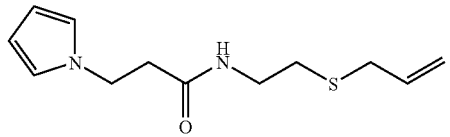

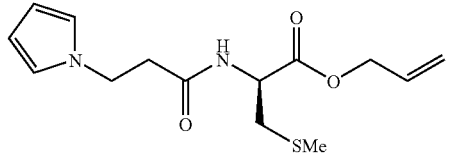

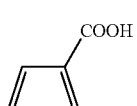

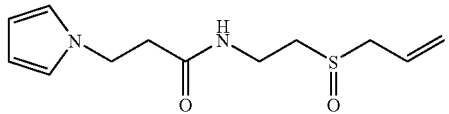

Poly A, poly G, poly L and poly R are outside the scope of the present invention, and are included as comparative examples. Medical devices coated with poly E, poly P and poly T are within the present invention. Poly E is discussed in detail below. Poly P and poly T are further examples of the present invention.

Electropolymerisation

Monomers for forming polymeric coatings on medical devices according to the present invention were electropolymerised according to well established procedures (2). Surface preparation of the discs, rods or stents before electrochemical coating involves, for example, degreasing with a commercial halocarbon, sonication in water for 5 minutes followed by washing with ethanol and drying. The amount of polymer on the metal surface was determined by weighing, by measuring the charge required for oxidising the polymer film or by measuring the bulk charge required to grow the film. The films were spectroscopically characterised by diffuse reflectance FTIR spectroscopy (3) when grown on discs.

The procedure for coating a stent with poly E is as follows. In their unexpanded state the stents used were 15 by 1.57 mm, with surface area of approximately 0.31 cm², made from 316 LVM stainless steel.

Prior to coating the stents underwent a strict preparation protocol. Following sonication in ethanol (>99.7% purity) for two hours and drying under a stream of compressed air, the stents were weighed on a five figure balance. They were further cleaned by dipping in concentrated nitric acid for 15 seconds. The acid was removed by soaking in ethanol. The stents were again dried under a stream of compressed air. The last cleaning step was to thoroughly spray with ZeroTri degreaser (LPS Laboratories, USA), and then dry.

The stents were transferred to an H-type cell containing 4-6 mM monomer E in a dinitrogen sparged 200 mM tetrabutyl ammonium tetra fluoroborate in dry acetonitrile solution, such that the entire length of the stent was under the surface of the solution and formed the working anode of the cell. The stent was held at a potential of about 1.1V versus the Ag/AgCl reference electrode and sufficient charge was passed to provide the desired coating thickness. After coating, the stent holder assembly was removed from the cell, and the stent placed in a bath of warm acetonitrile to remove residual electrolyte. The stent was then removed, dried and re-weighed to give an estimation of coating weight.

Platelet Adhesion and Activation

Poly E and poly R were formed as polymer coatings on the surface of a medical steel disc of diameter 1 cm. Poly E is within the present invention, poly R is a comparative example. The platelet adhesion and activation properties of steel coated with poly E and with poly R were compared with those of uncoated 316 LVM medical steel.

Platelet rich plasma (PRP) was retrieved from whole citrated human blood by gentle centrifugation at 200 g for 10 minutes. The PRP was then diluted 50:50 in sterile phosphate buffered saline (PBS) containing 5.5 mM of glucose (warmed to 37° C.) and 0.5 mL of this was added to each steel sample (coated with poly E, coated with poly R, uncoated). The samples were then incubated at 37° C. under an atmosphere of 5% $CO_2$ for one hour. After incubation, the samples were rinsed three times in PBS to remove any non-adherent platelets. The samples were then fixed in 2.5% SEM grade glutaraldehyde (in cocadylate buffer) for two hours at room temperature. After fixation the samples were dehydrated through a series of increasing concentrations of ethanol (30, 50, 70, 90 and 100%) for 15 minutes at each concentration. The samples were then air dried, mounted and sputter coated with palladium for SEM analysis.

The number of platelets were counted per field of view (100 μm×140 μm), and the average calculated from ten fields of view per sample on three replicate samples. Platelet shapes have bee categorised into either spread (activated) or round (non-activated). Previous studies have similarly identified various stages of platelet morphological changes upon adhesion to foreign surfaces (4,5). It is commonly assumed that platelet shape changes are strongly associated with activation.

FIG. 1 provides an indication of the number and morphology of adherent platelets to each material tested. These results clearly suggest that coating poly E reduces both platelet adhesion and platelet activation compared with bare steel. Also it can be seen that the poly E coated steel has significantly lower platelet adhesion than poly R coated steel. These results suggest that polymer coatings on medical devices according to the present invention significantly reduce platelet adhesion and activation, and therefore are likely to significantly reduce the thrombogenicity of such devices.

Endothelialisation

Figure 2:
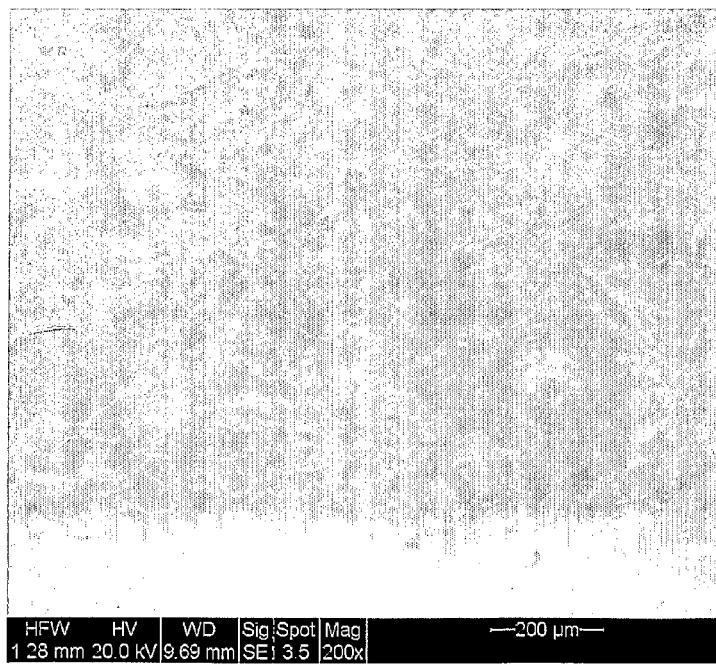
FIG. 2 is a photomicrograph showing a lawn of coronary endothelial cells on a polymer coated stainless steel disc.

As discussed above, the ability of a coating to support endothelialisation is a desirable feature in implantable devices, particularly stents. The ability of poly E to support the growth of human coronary endothelial cells is shown by the photomicrograph in FIG. 2. FIG. 2 shows a monolayer lawn of coronary endothelial cells laid down on a 1 cm diameter stainless steel disc coated with approximately 1 μm layer of poly E.

General In Vivo Tolerance

Poly A, poly E, poly G and poly R coatings on stainless steel rods were implanted into rabbit dorsal muscle together with uncoated 316L stainless steel controls. These were removed and examined after implantation for periods up to 90 days as defined by EN 10993-6. The results showed that the polymers were very well tolerated and that poly E in particular behaved better than the bare metal control with respect to fibrin formation as shown in Table 1.

TABLE 1

Tolerance of poly E in rabbits following muscular implantation: histological findings, summary of biological parameters

|  | Kill Day 31 | | Kill Day 61 | | Kill Day 91 | |
| --- | --- | --- | --- | --- | --- | --- |
|  | Control sites | Test sites | Control sites | Test sites | Control sites | Test sites |
| Total examined Fibroplasia | (11) | (11) | (12) | (12) | (11) | (12) |
| minimal | 1 | 8 | 7 | 9 | 8 | 12 |
| mild | 7 | 3 | 3 | 3 | 3 | 0 |
| moderate | 3 | 0 | 1 | 0 | 0 | 0 |
| Total | 11 | 11 | 11 | 12 | 11 | 12 |
| Myofibre degeneration | 8 | 1 | 2 | 0 | 3 | 1 |
| Lymphocytic infiltration | 4 | 4 | 2 | 7 | 1 | 3 |
| Polymorphonuclear infiltration | 0 | 1 | 1 | 3 | 0 | 1 |
| Mononuclear cell infiltration | 1 | 0 | 0 | 0 | 0 | 0 |
| Pigmented macrophages | 3 | 1 | 1 | 6 | 0 | 8 |
| Giant cells | 4 | 2 | 0 | 1 | 1 | 0 |
| Mineralisation | 4 | 6 | 0 | 5 | 0 | 1 |
| Fibrosis (distant from implant site) | 5 | 2 | 4 | 5 | 2 | 0 |

Cytotoxicity

The very low cytotoxicity of polypyrroles, including those usable in the present invention, is illustrated by the data obtained for poly E. The assay protocol used MRC-5 cells followed by the procedure defined by ISO 10993 with polyethylene and latex rubber as the negative and positive controls respectively. The results in Table 2 illustrate that poly E extracts showed no resulting cell damage to the sensitive strain.

TABLE 2

| Dose Level | Polyethylene | | | Latex Rubber | | | Poly E | | |
| --- | --- | --- | --- | --- | --- | --- | --- | --- | --- |
| (% eluate added) | Sample 1 | Sample 2 | Sample 3 | Sample 1 | Sample 2 | Sample 3 | Sample 1 | Sample 2 | Sample 3 |
| 0 | 0 | 0 | 0 | 0 | 0 | 0 | 0 | 0 | 0 |
| 6.25 | 0 | 0 | 0 | 4 | 4 | 4 | 0 | 0 | 0 |
| 12.5 | 0 | 0 | 0 | 4 | 4 | 4 | 0 | 0 | 0 |
| 25 | 0 | 0 | 0 | 4 | 4 | 4 | 0 | 0 | 0 |

TABLE 2-continued

| Dose Level | Polyethylene | | | Latex Rubber | | | Poly E | | |
|---|---|---|---|---|---|---|---|---|---|
| (% eluate added) | Sample 1 | Sample 2 | Sample 3 | Sample 1 | Sample 2 | Sample 3 | Sample 1 | Sample 2 | Sample 3 |
| 50 | 0 | 0 | 0 | 4 | 4 | 4 | 0 | 0 | 0 |
| 100 | 0 | 0 | 0 | 4 | 4 | 4 | 0 | 0 | 0 |

Grading of toxicity:
0 = No cells showing damage
1 = 0-25% of cells showing damage
2 = 25-50% of cells showing damage
3 = 50-75% of cells showing damage
4 = 75-100% of cells showing damage Haemocompatibility Poly A and poly E were tested for haemocompatibility under the ISO 10993 guidelines for medical implants. Both were found to be haemocompatible, as shown in table 3.

TABLE 3

Haemocompatibility Index (% Haemolysis)

| sample | Donor Blood A | Donor Blood B | Donor Blood C | Mean | Haemolytic grade |
|---|---|---|---|---|---|
| poly A | 0.0 | 0.0 | 0.0 | 0.0 | Non-haemolytic |
| poly E | 0.0 | 0.0 | 0.0 | 0.0 | Non-haemolytic |
| Saline | 0.0 | 0.0 | 0.0 | 0.0 | Non-haemolytic |
| Saponin | 84.0 | 86.0 | 57.8 | 75.9 | Severely haemolytic |

Adhesion Studies

Adhesion of the polymers unmodified polypyrrole, poly A, poly L and poly E to 316L polished stainless steel (surface roughness factor $R_a$=0.03) was tested by TWI. The force per unit area required to fracture a cyanoacrylate bonded steel stub from the polymer-coated 316L stainless steel plaque was measured, and the results obtained are as shown in Table 4.

TABLE 4

| Polymer | Force per unit area/MPa |
|---|---|
| Polypyrrole (unmodified) | <1 |
| Poly A | 2.4 |
| Poly L | 3.9 |
| Poly E | >6.7 |

Therefore, it can be seen that polymer coatings according to the present invention (poly E) showed very strong adhesion to steel. This is desirable because it reduces the risk of the polymer coating flaking off or otherwise cracking or breaking which can lead to thrombosis or other undesirable effects.

Figure 3:
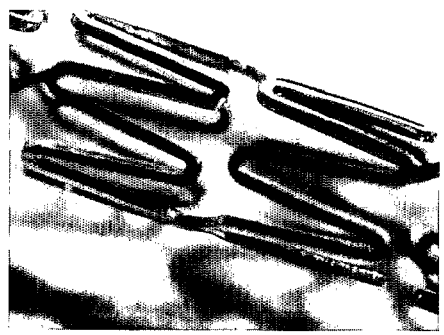
FIG. 3 shows a coated stent according to the present invention after incubation in saline at 37° C. for 14 days with 30 rpm shaking.

Five stainless steel stents coated with poly E were incubated at 37° C. in blood isotonic saline solution for 14 days, with 30 rpm shaking. They were removed and photomicrographs were taken. No flaws, cracking or flaking of the coatings was observed at 20 nm resolution. FIG. 3 shows a stent treated as described.

Figure 4:
FIG. 4 shows an expanded stent according to the present invention coated with poly E.
Figure 5:
FIG. 5 is a close-up view of a strut of the stent in FIG. 4.

Three stainless steel stents coated with poly E were each manually crimped onto a catheter balloon which was then fully expanded. The coated stents were removed and photomicrographs were taken. No flaws, cracking or flaking of the coatings was observed at 20 nm resolution. This demonstrates the physical robustness of the polymer coating. FIG. 4 shows an expanded stent coated with poly E. FIG. 5 is a close-up view of a strut of the stent.

In Vivo Tests

As mentioned above, the occurrence of late-onset thrombosis in use of drug-eluting stents has caused bare metal stents to be favoured. In vivo tests carried out in pig coronary arteries using stents coated with a coating layer in accordance with the present invention have shown that such stents induce no adverse vascular response compared to bare metal stents.

Method: Stents with a ca. 1 µm thick polymer surface layer formed by electropolymerisation of the functionalised pyrrole monomer E (N,N'-Bis[3-(pyrrol-1-yl)propanoyl]-L-cystine diallyl ester) described above (Coated stents) and bare metal stents (BMS) were implanted into native coronary arteries of 17 farm pigs by standard endovascular technique (26 Coated stents, 25 BMS stents). The stents were made of 316 L stainless steel. The electropolymerisation was carried out as described in reference 2 (Le Gall et al.). At one week post-implant 6 stented arteries (N=6) and at one month post-implant 11 stented arteries (N=11) were taken for analysis. Results: Coated stents evoked response indistinguishable from BMS at 1-week. For 1-month implants, there were no differences in intima thickness (coated 0.28±0.18 vs. BMS 0.25±1.18 mm, P=NS) or % area stenosis (coated 37±19 vs. BMS 32±20%, P=NS). Both stent types were endothelialized and vessel morphology was similar. Conclusion: Novel stent surface modification by introduction of an allyl cystine surface motif attached to a poly(pyrrole) backbone formed by electropolymerisation evokes a coronary artery response indistinguishable from bare metal stents in pig coronaries.

Syntheses

Monomer A 3-(Pyrrol-1-yl)propanoic acid was prepared according to a modification of literature procedures (6,7). Tetrabutyl ammonium hydroxide solution (1.0 M in methanol, 15.4 mL, 15.4 mmol, 0.1 equiv.) was added to pyrrole (10 g, 154 mmol, 1 equiv.) with stirring under nitrogen. Acrylonitrile (30 mL, 786.5 mmol, 5.3 equiv) was added very slowly over 2.5 hours, keeping the temperature below 50° C. The reaction was then allowed to stir for a further hour at room temperature before the addition of potassium hydroxide (30 g, 535 mmol, 3.5 equiv.) in distilled water (45 mL) and refluxing for 1.75 hours. After cooling to room temperature, the pH of the reaction mixture was lowered to 5.5 by the addition of 2M hydrochloric acid (ca. 70 mL) and then the resultant solution extracted with diethyl ether (100 mL). After a single extraction, the pH of the aqueous phase was again lowered to 5.5 followed by a further extraction with diethyl ether (100 mL). This acidification and extraction process was repeated approx. 15 to 20 times. The combined organic washings were dried ($MgSO_4$) and the solvent evaporated in vacuo to yield an off white crystalline solid (10.1 g, 47%). $v_{max}$ (KBr disc) 2922 (N—H), 1700 (C=O) cm$^{-1}$; δ (400 MHz, $CDCl_3$) 6.67 (2H, t, J 2.1 Hz, C(α)H pyrrole), 6.14 (2H, t, J 2.1 Hz, C(β)H pyrrole), 4.20 (2H, t, J 6.8 Hz, py-CH$_2$—), 2.82 (2H, t, J 6.8 Hz, —CH$_2$COOH).

Monomer E

In a modified literature procedure (2) CDI (carbodiimidazole, 3.00 g, 18 mmol, 2.2 equiv) was added to a solution of 3-(pyrrole-1-yl) propanoic acid (2.66 g, 18 mmol, 2.2 equiv.) in dry THF (40 mL) and the reaction mixture stirred for 1.5 hours under nitrogen at room temperature. Meanwhile, L-cystine bisallyl ester bis(toluene-4-sulphonate) (6.00 g, 8.2 mmol, 1 equiv.) was dissolved in THF (60 mL) with stirring under nitrogen, with the dropwise addition of sufficient triethylamine to effect the dissolution. The ester solution was then added to the activated acid solution by cannula. The resultant reaction mixture was stirred at room temperature for 68 hours followed by warming to 60° C. for a further 6 hours. Once cool, the solvent was evaporated under vacuum to yield a yellow oily solid. The pure product was obtained was a white solid by washing with DCM and further recrystallisation of the mother liquor from DCM/diethyl ether. White crystalline solid (m.p. 164-5° C.). Found C, 55.50; H, 6.19; N, 9.82. $C_{26}H_{34}N_4O_6S_2$ requires C, 55.50; H, 6.09; N, 9.96%. $v_{max}$ (Nujol®) 3315 (N—H), 1733 (C=O ester), 1640 (C=O amide), 1537 (C=O amide), 731 (C—H) cm$^{-1}$; δ (400 MHz, CDCl$_3$) 6.62 (4H, t, J 2.0 Hz, C(α)H pyrrole), 6.31 (2H, d, J 7.3 Hz, NH), 6.08 (4H, t, J 2.0 Hz, C(β)H pyrrole), 5.83 (2H, m, —CH=CH$_2$), 5.28 (4H, m, —CH=CH$_2$), 4.80 (2H, m, —CHCH$_2$S—), 4.61 (4H, t, J 3.0 Hz, —OCH$_2$CH=CH$_2$), 4.17 (4H, m, py-CH$_2$—), 2.99 (4H, m, —CH$_2$S—), 2.63 (4H, t, J 6.7 Hz, py-CH$_2$CH$_2$—).

Monomer G

N,N'-Bis[3-(pyrrol-1-yl)propanoyl]-L-cystine dimethyl ester was prepared according to a literature procedure (3). White solid (m.p. 146-147° C.). Found C, 51.70; H, 5.75; N, 11.00. $C_{22}H_{30}N_4O_6S_2$ C, 51.75; H, 5.92; N, 10.97%. $v_{max}$ 3327 (N—H), 1739 (C=O ester), 1643 (C=O amide) cm$^{-1}$; δ (270 MHz, CDCl$_3$) 6.63 (4H, t, J 2.0 Hz, C(α)H pyrrole), 6.36 (2H, d, J 7.3 Hz, NH), 6.09 (4H, t, J 2.0 Hz, C(β)H pyrrole), 4.79 (2H, td, J 7.5 Hz, J' 5.1 Hz, —CHCH$_2$S—), 4.21 (4H, dt, J 6.7 Hz, J' 2.6 Hz, py-CH$_2$—), 3.73 (6H, s, —OCH$_3$), 3.10 (2H, dd, J 14.5 Hz, J' 5.1 Hz, —CH(H)S—), 3.00 (2H, dd, J 14.3 Hz, J' 5.1 Hz, —CH(H)S—), 2.67 (4H, t, J 6.8 Hz, py-CH$_2$CH$_2$—).

Monomer L

N-(2-Mercapto-ethyl)-3-pyrrol-1-yl-propionamide (1.3 g, 6.52 mmol, 1 equiv.) was dissolved in acetonitrile (80 mL) with stirring under nitrogen. Triethylamine (2.7 mL, 1.96 g, 19.4 mmol, 3 equiv.) was added dropwise followed by allyl bromide (0.6 mL, 838.8 mg, 6.93 mmol, 1.06 equiv.) and the reaction refluxed for 10 hours. After cooling, the white precipitate by product that had formed was removed by filtration and the solvent evaporated to yield the crude product. Further by product was removed by stirring with ethyl acetate (100 mL) and again filtering off the solid. Removal of the solvent in vacuo and purification by flash chromatography on silica eluting with ethyl acetate ($R_f$ 0.55) afforded pure N-(2-Mercapto-ethyl)-3-pyrrol-1-yl-propionamide as a yellow solid.

Monomer P

To a stirred solution of pyrrole propanoic acid (0.8 g, 5.75 mmol) in thf (20 ml), 1-1' carbonyl diimidazole (1 g, 6.2 mmol) was added portion wise and the mixture was left stirring for 1 h. Methionine allyl ester (2.3 g, 6.4 mmol) in thf (30 ml) was then added along with Et$_3$N. The reaction mixture was stirred for 8 h at room temperature. All solvent was removed under vacuum, and the product was extracted by Et$_2$O. The Et$_2$O phase was evaporated under vacuum. The solid was washed with hexane to give a white solid 1.2 g (4 mmol) 63% yield. $v_{max}$ (Nujol®) 3314 (N—H), 1745 (C=O ester), 1634 (C=O amide), 1532 (C=O amide) cm$^{-1}$; δ (400 MHz, CD$_3$CN) 6.81 (1H, br s, NH), 6.64 (2H, t, J 2.1 Hz, C(α)H pyrrole), 5.99 (2H, t, J 2.0 Hz, C(β)H pyrrole), 5.96-5.86 (1H, m, —CH=CH$_2$), 5.31 (1H, m, —CH=C(H)Htrans), 5.21 (1H, m, —CH=C(H)Hcis), 4.57 (2H, d, 5.6 Hz, py-CH$_2$—), 4.52-4.47 (1H, m, —CHCH$_2$S—), 4.15-4.12 (2H, m, —OCH$_2$CH=CH$_2$), 2.70-2.55 (2H, m, —CH$_2$S—), 2.47-2.37 (2H, m, py-CH$_2$CH$_2$—), 2.01 (3H, s, —SCH$_3$); m/z (E.I.) 310 (M$^+$).

Monomer R

This material is commercially available (Aldrich).

Monomer T

N-(2-Allylsulfanyl-ethyl)-3-pyrrol-1-yl-propionamide (0.3704 g, 1.554 mmol, 1 equiv) was taken up in 100 ml of dichloromethane with stirring under nitrogen. The reaction mixture was cooled to between 0-4 C. Meta-chloroperoxybenzoic acid (0.4815 g, 2.790 mmol, 1.8 equiv) was added to the mixture and the reaction stirred at 0-4 C for 16 hours. The solvent was removed in vacuo and purification by flash chromatography on silica: eluting with ethyl acetate gave the by-product meta-chlorobenzoic acid. Further elution with the solvent mixture was gradually changed to a 1:1 ethyl acetate/ ethanol gave the product which was isolated by removal of the solvent in vacuo as off-white crystals in 60% yield.

δ (300 MHz, CDCl$_2$) 6.58 (2H, t, J 1.9 Hz, C(α)H pyrrole), 6.38 (1H, br s, NH), 6.04 (2H, t, J 2.1 Hz, C(β)H pyrrole), 5.76 (1H, m, —CH=CH$_2$), 5.41-5.30 (2H, m, —CH=CH$_2$), 4.15 (2H, t, J 6.5 Hz, py-CH$_2$—), 3.65 (2H, q, J 6.0 Hz, —NHCH$_2$), 3.48 (2H, m, —CH$_2$CH=CH$_2$), 2.81 (2H, m, —NHCH$_2$CH$_2$S—), 2.52 (2H, t, J 6.6 Hz, py-CH$_2$CH$_2$—) m/z (E.S.) 254.85 (M$^+$).

REFERENCES

1. Kiesewetter H et al. Effect of garlic on platelet aggregation in patients with increased risk of juvenile ischemic attack. *J. Clin. Pharm.* 1993: 45(4); 333-336.
2. Le Gall et al. Synthesis of N-derivatised pyrroles: precursors to highly functionalised electropolymers. *J. Chem. Soc. Perkin Trans.* 1999: 1; 1657-1664.
3. Pickett C J and Ryder K S. Bioinorganic reaction centres on electrodes—modified electrodes possessing amino-acid, peptide and ferredoxin-type groups on a poly(pyrrole) backbone. *J. Chem. Soc. Dalton Trans.* 1994: 14; 2181-2189.
4. Frank R D et al. Glutardialdehyde induced fluorescence technique (GIFT): A new method for the imaging of platelet adhesion on biomaterials. *J. Biomed. Mat. Research.* 2000: 52; 374-381.
5. Ko T M et al. Surface characterisation and platelet adhesion studies of plasma-sulphonated polyethylene. *Biomaterials.* 1993: 14(9); 657-664.
6. Blume R C at al. Formylation and cyanoethylation of substituted idoles. *J. Org. Chem.* 1945: 10(3); 255-258.
7. Kashiwagi Y et al. Polypyrrole-supported graphite felt for acetylene coupling reaction in solid phase. *Synlett.* 2004: 14; 2513-2516.

The invention claimed is:

1. A medical device having a surface which in use contacts body tissue, wherein said surface has on it a biocompatible coating layer comprising a polymer having allyl-terminated pendent groups covalently attached to the polymeric chain, said pendent groups comprising a moiety selected from the group consisting of: —O—CH$_2$—CH=CH$_2$; —S—CH$_2$—CH=CH$_2$; and —S(=O)—CH$_2$—CH=CH$_2$; and wherein the polymer is an electropolymerized polymer.

2. A medical device according to claim 1 wherein said pendent groups comprise a moiety selected from the group consisting of: —C(=O)—o—CH$_2$—CH=CH$_2$: —CH$_2$—S(=O)—CH$_2$—CH=CH$_2$; —S—S—CH$_2$CH=CH$_2$; —S(=O)—S—CH$_2$CH=CH$_2$: and —S—(=O)—CH$_2$CH=CH$_2$.

3. A medical device according to claim 1 wherein the pendent group is bound to the polymer via an amido, ester or ether moiety.

4. A medical device according to claim 1 wherein the polymer is formed by polymerisation of one or more types of monomer, at least one of the types of monomer comprising said pendent group.

5. A medical device according to claim 1, wherein the polymer is selected from the group consisting of a polypyrrole, a polythiophene and a polyanilines.

6. A medical device according to claim 1 wherein the surface of the medical device is a conductive surface.

7. A medical device according to claim 6 wherein the conductive surface is a metal surface.

8. A medical device according to claim 1 wherein the medical device is selected from the group consisting of a stent, an orthopaedic implant, a pump, a heart valve, a blood dialysis device, a blood storage container, and a catheter guide wire.

9. A medical device according to claim 1 wherein the medical device is adapted to be implanted in a mammalian body.

10. A medical device according to claim 2 wherein the pendent group is bound to the polymer via a moiety selected from the group consisting of amido, ester and ether moieties.

11. A medical device according to claim 2 wherein the polymer is formed by polymerisation of one or more types of monomer, at least one of the types of monomer comprising said pendent group.

12. A method of manufacture of a medical device comprising the step of forming a biocompatible polymeric layer by electropolymerisation of one or more types of monomer, wherein at least one of the types of monomer includes a covalently bound allyl-terminated pendent group, said pendent group comprising a moiety selected from the group consisting of: —O—CH$_2$—CH=CH$_2$; —S—CH$_2$=CH$_2$; and —S(=O)—CH$_2$—CH=CH$_2$.

13. A method of decreasing the occurrence of late-onset thrombosis, the method comprising contacting body tissue with the medical device of claim 1.

14. The method of according to claim 13 wherein the medical device is implanted in body tissue.

* * * * *